US010485846B2

(12) United States Patent
Herman et al.

(10) Patent No.: US 10,485,846 B2
(45) Date of Patent: Nov. 26, 2019

(54) COLLAGENASE-DERIVED PEPTIDES PROMOTE TISSUE REGENERATION AND WOUND HEALING

(71) Applicant: Tufts University, Medford, MA (US)

(72) Inventors: Ira M. Herman, Boston, MA (US); Tatiana Demidova-Rice, Malden, MA (US)

(73) Assignee: Tufts University, Medford, MA (US)

( * ) Notice: Subject to any disclaimer, the term of this patent is extended or adjusted under 35 U.S.C. 154(b) by 0 days.

(21) Appl. No.: 15/534,140

(22) PCT Filed: Dec. 11, 2015

(86) PCT No.: PCT/US2015/065181
§ 371 (c)(1),
(2) Date: Jun. 8, 2017

(87) PCT Pub. No.: WO2016/094764
PCT Pub. Date: Jun. 16, 2016

(65) Prior Publication Data
US 2018/0339013 A1    Nov. 29, 2018

Related U.S. Application Data

(60) Provisional application No. 62/091,444, filed on Dec. 12, 2014.

(51) Int. Cl.
| | | |
|---|---|---|
| *A61K 38/10* | (2006.01) |
| *A61K 38/18* | (2006.01) |
| *A61K 38/19* | (2006.01) |
| *A61K 38/43* | (2006.01) |
| *C12N 9/64* | (2006.01) |
| *A61K 38/39* | (2006.01) |
| *C07K 14/78* | (2006.01) |
| *C07K 14/47* | (2006.01) |
| *C07K 14/485* | (2006.01) |
| *A61P 17/02* | (2006.01) |
| *A61K 38/08* | (2019.01) |
| *A61K 38/48* | (2006.01) |
| *C07K 7/06* | (2006.01) |
| *C07K 7/08* | (2006.01) |

(52) U.S. Cl.
CPC ............. *A61K 38/10* (2013.01); *A61K 38/08* (2013.01); *A61K 38/18* (2013.01); *A61K 38/19* (2013.01); *A61K 38/39* (2013.01); *A61K 38/43* (2013.01); *A61K 38/4886* (2013.01); *A61P 17/02* (2018.01); *C07K 7/06* (2013.01); *C07K 7/08* (2013.01); *C07K 14/47* (2013.01); *C07K 14/472* (2013.01); *C07K 14/485* (2013.01); *C07K 14/78* (2013.01); *C12N 9/6491* (2013.01); *C12Y 304/24007* (2013.01); *C07K 2319/00* (2013.01); *C07K 2319/50* (2013.01)

(58) Field of Classification Search
CPC .... A61K 2300/00; A61K 38/18; A61K 38/19; A61K 38/43; A61K 38/08; A61K 38/10; A61K 38/39; A61K 38/4886; A61P 17/02; C07K 14/47; C07K 14/472; C07K 14/485; C07K 14/78; C07K 2319/00; C07K 7/06; C07K 7/08; C07K 2319/50; C12N 9/6491; C12Y 304/24007

See application file for complete search history.

(56) References Cited

U.S. PATENT DOCUMENTS

| | | | |
|---|---|---|---|
| 8,586,006 B2 * | 11/2013 | Hood | G01N 33/6845 424/1.11 |
| 2006/0051774 A1 | 3/2006 | Dahary et al. | |
| 2007/0219125 A1 * | 9/2007 | Cojocaru | C07K 14/78 424/130.1 |
| 2012/0087862 A1 | 4/2012 | Hood et al. | |

FOREIGN PATENT DOCUMENTS

| | | | | |
|---|---|---|---|---|
| WO | WO 1992/13887 | | 8/1992 | |
| WO | WO01/88122 | * | 5/2000 | ............. C12N 15/11 |

OTHER PUBLICATIONS

Ambily et al., The role of plasma membrane STIM1 and Ca(2+)entry in platelet aggregation. STIM1 binds to novel proteins in human platelets. Cell Signal. Mar. 2014;26(3):502-11. doi: 10.1016/j.cellsig.2013.11.025. Epub Dec. 2, 2013.
Demidova-Rice et al., Bioactive peptides derived from vascular endothelial cell extracellular matrices promote microvascular morphogenesis and wound healing in vitro. Wound Repair Regen. Jan.-Feb. 2011;19(1):59-70. doi: 10.1111/j.1524-475X.2010.00642.x. Epub Dec. 6, 2010.
Demidova-Rice et al., Human platelet-rich plasma—and extracellular matrix-derived peptides promote impaired cutaneous wound healing in vivo. PLoS One. 2012;7(2):e32146. doi: 10.1371/journal.pone.0032146. Epub Feb. 23, 2012.
Gomes et al., Wound-Healing Peptides for Treatment of Chronic Diabetic Foot Ulcers and Other Infected Skin Injuries. Molecules. Oct. 18, 2017;22(10). pii: E1743. doi: 10.3390/molecules22101743.
Sheets et al., Identification and Characterization of Novel Matrix-Derived Bioactive Peptides: A Role for Collagenase from Santyl® Ointment in Post-Debridement Wound Healing? PLoS One. Jul. 26, 2016;11(7):e0159598. doi: 10.1371/journal.pone.0159598. eCollection 2016.

(Continued)

*Primary Examiner* — Marcela M Cordero Garcia
(74) *Attorney, Agent, or Firm* — Wolf, Greenfield & Sacks, P.C.

(57) ABSTRACT

Provided herein are methods and compositions for the treatment of wounds in a mammalian subject. Particularly, novel bioactive polypeptides are provided that promote tissue repair and regeneration, including the activation of/stimulation of wound healing and wound closure, stimulate keratinocyte and endothelial cell motility and/or proliferation.

23 Claims, 9 Drawing Sheets

Specification includes a Sequence Listing.

(56) References Cited

OTHER PUBLICATIONS

Tallis et al., Clinical and economic assessment of diabetic foot ulcer debridement with collagenase: results of a randomized controlled study. Clin Ther. Nov. 2013;35(11):1805-20. doi: 10.1016/j.clinthera.2013.09.013. Epub Oct. 18, 2013.

* cited by examiner

```
                          SEQUENCE LISTING

<160> NUMBER OF SEQ ID NOS: 19

<210> SEQ ID NO 1
    <211> LENGTH: 14
    <212> TYPE: PRT
    <213> ORGANISM: Homo sapiens

<400> SEQUENCE: 1

Asn Phe Gln Gly Val Gln Asn Arg Phe Val Phe Gly Thr Pro
    1               5                   10

<210> SEQ ID NO 2
    <211> LENGTH: 16
    <212> TYPE: PRT
    <213> ORGANISM: Homo sapiens

<400> SEQUENCE: 2

Met Glu Asn Ala Glu Leu Asp Val Pro Ile Gln Ser Val Phe Thr Arg
    1               5                   10                  15

<210> SEQ ID NO 3
    <211> LENGTH: 11
    <212> TYPE: PRT
    <213> ORGANISM: Homo sapiens

<400> SEQUENCE: 3

Asn Thr Asp Asn Ile Tyr Pro Glu Ser Ser Cys
    1               5                   10

<210> SEQ ID NO 4
    <211> LENGTH: 8
    <212> TYPE: PRT
    <213> ORGANISM: Homo sapiens

<400> SEQUENCE: 4

Pro Tyr Leu Gly Tyr Val Phe Lys
    1               5

<210> SEQ ID NO 5
    <211> LENGTH: 18
    <212> TYPE: PRT
    <213> ORGANISM: Homo sapiens

<400> SEQUENCE: 5

Met Gln Thr Val Ala Gln Leu Phe Lys Thr Val Ser Ser Leu Ser Leu
    1               5                   10                  15

Ser Thr
```

```
<210> SEQ ID NO 6
<211> LENGTH: 19
<212> TYPE: PRT
<213> ORGANISM: Homo sapiens

<400> SEQUENCE: 6

His Ser Pro Asp Ile Gln Leu Gln Lys Gly Leu Thr Phe Glu Pro Ile
1               5                   10                  15

Gln Ile Lys

<210> SEQ ID NO 7
<211> LENGTH: 16
<212> TYPE: PRT
<213> ORGANISM: Homo sapiens

<400> SEQUENCE: 7

Ser Thr Ile Thr Gln Pro Tyr Lys Thr Leu Asn Asn Ala Arg Ser Pro
1               5                   10                  15

<210> SEQ ID NO 8
<211> LENGTH: 16
<212> TYPE: PRT
<213> ORGANISM: Homo sapiens

<400> SEQUENCE: 8

Arg Pro Gly Pro Ser Pro Glu Gly Thr Gly Gln Ser Tyr Asn Tyr Arg
1               5                   10                  15

<210> SEQ ID NO 9
<211> LENGTH: 16
<212> TYPE: PRT
<213> ORGANISM: Homo sapiens

<400> SEQUENCE: 9

Met Glu Asn Ala Glu Leu Asp Pro Pro Tyr Leu Gly Tyr Val Phe Lys
1               5                   10                  15

<210> SEQ ID NO 10
<211> LENGTH: 20
<212> TYPE: PRT
<213> ORGANISM: Homo sapiens

<400> SEQUENCE: 10

Thr Gly Gln Ser Tyr Asn Gln Tyr Ser Gln Arg Pro Tyr Leu Gly Val
1               5                   10                  15

Tyr Val Phe Lys
            20

<210> SEQ ID NO 11
<211> LENGTH: 10
<212> TYPE: PRT
<213> ORGANISM: Homo sapiens

<400> SEQUENCE: 11

Leu Tyr Gly Gln Thr Pro Leu Glu Thr Leu
1               5                   10

<210> SEQ ID NO 12
<211> LENGTH: 11
<212> TYPE: PRT
<213> ORGANISM: Homo sapiens

<400> SEQUENCE: 12

Glu Leu Ala Asp Ser Pro Ala Leu Glu Ile Gly
```

```
                1               5                       10

<210> SEQ ID NO 13
<211> LENGTH: 21
<212> TYPE: PRT
<213> ORGANISM: Homo sapiens

<400> SEQUENCE: 13

Leu Tyr Gly Gln Thr Pro Leu Glu Thr Leu Glu Leu Ala Asp Ser Pro
1               5                   10                  15

Ala Leu Glu Ile Gly
            20

<210> SEQ ID NO 14
<211> LENGTH: 14
<212> TYPE: PRT
<213> ORGANISM: Homo sapiens

<400> SEQUENCE: 14

Val Ser Gly Asn Thr Val Glu Tyr Ala Leu Pro Thr Leu Glu
1               5                   10

<210> SEQ ID NO 15
<211> LENGTH: 18
<212> TYPE: PRT
<213> ORGANISM: Homo sapiens

<400> SEQUENCE: 15

Leu Asp Ser Pro Thr Ala Pro Thr Val Gln Ser Thr Ala Leu Thr Trp
1               5                   10                  15

Arg Pro

<210> SEQ ID NO 16
<211> LENGTH: 17
<212> TYPE: PRT
<213> ORGANISM: Homo sapiens

<400> SEQUENCE: 16

Leu Asp Gly Ser Ala Pro Gly Pro Leu Tyr Thr Gly Ser Ala Leu Asp
1               5                   10                  15

Phe

<210> SEQ ID NO 17
<211> LENGTH: 11
<212> TYPE: PRT
<213> ORGANISM: Homo sapiens

<400> SEQUENCE: 17

Gly Ser Glu Gly Val Arg Ser Gly Arg Ser Gly
1               5                   10

<210> SEQ ID NO 18
<211> LENGTH: 14
<212> TYPE: PRT
<213> ORGANISM: Homo sapiens

<400> SEQUENCE: 18

Gln Pro Gln Pro Leu Pro Ser Pro Gly Val Gly Gly Lys Asn
1               5                   10

<210> SEQ ID NO 19
<211> LENGTH: 11
<212> TYPE: PRT
```

```
<213> ORGANISM: Homo sapiens

<400> SEQUENCE: 19

Lys Tyr Thr Leu Asn Pro Val Ile Asp Ala Ser
1               5                   10
```

COLLAGENASE-DERIVED PEPTIDES PROMOTE TISSUE REGENERATION AND WOUND HEALING

RELATED APPLICATION

This application is a national stage filing under 35 U.S.C. § 371 of International Application No. PCT/US2015/065181, filed Dec. 11, 2015, entitled "Collagenase-Derived Peptides Promote Tissue Regeneration and Wound Healing, and claims the benefit under 35 U.S.C. § 119(e) of U.S. Provisional Application Ser. No. 62/091,444, filed on Dec. 12, 2014, the entire disclosure of each of which is incorporated by reference herein in its entirety.

BACKGROUND

Wound healing is a complex, highly-coordinated process that begins and ends with tissue remodeling. The extracellular matrix and its associated growth regulatory substances play a pivotal role in dynamically and reciprocally regulating the cellular response and wound healing. Initially believed to be solely important as an early component of the provisional, blood-borne matrix, the enzymes and structural macromolecules of the extracellular matrix cooperate with cytokines and growth factors, yielding a dynamic that orchestrates healing (1-7).

Wound healing and chemotactic properties of peptides obtained by collagenase-digestion of collagen have been known since the late 1970s. See, Postlethwaite et al., Proceedings of the National Academy of Science, 75:871-875 (1978).

Under normal circumstances, the process of acute wound healing can be broken down into three phases. An initial inflammatory phase, which is followed by robust tissue remodeling and proliferation (the proliferative phase), is succeeded by a "maturational phase" wherein re-epithelialization, dermal angiogenesis and wound closure ensues. Re-epithelialization involves the migration and proliferation of epithelial tissue, primarily keratinocytes. Angiogenesis is the growth of new blood vessels from pre-existing conduits, and is regulated by a panoply of soluble cytokines including growth factor polypeptides, as well as cell-cell and cell-matrix interactions. Chronic wounds exhibit a different healing profile from normal acute wounds in that they generally remain in an inflamed state for protracted periods of time. Non-healing wounds can most commonly be observed amongst people with diabetes, venous stasis disease, and in those patients who are immobilized.

SUMMARY

In view of the foregoing, it would be desirable to provide new bioactive biomolecules that safely and efficiently potentiate epithelial and vascular wound healing mechanisms in both acute and chronic wound healing situations.

Provided herein are wound healing peptides, compositions containing such peptides, and methods for the promotion of wound healing. The peptides are resistant to the degrading and compromising action of the "hostile" environment, which typifies non-healing wounds. Prior attempts to develop advanced protein-based wound healing therapeutics have largely failed because the wound bed's robust protease profile degrades any bioactive protein entity that is delivered. For these reasons, bioactive wound healing peptides that are resistant to protease action are highly beneficial since the peptides promote tissue remodeling, angiogenesis and epithelialization despite the elevated protease profile present within the wounds. At the same time, activation of healing help to "re-equilibrate" the wound bed, thus potentially up-regulating protease inhibitors, down-regulating host proteases or both. In one aspect, an isolated peptide is provided that includes an amino acid sequence selected from the group consisting of SEQ ID NOs: 1-19. In some embodiments, the peptide includes less than 100, 95, 90, 85, 80 75, 70, 65, 60, 55, 50, 45, 40, 35, 30, 25 or 20 amino acids.

According to another aspect, an isolated peptide is provided that includes an amino acid sequence selected from the group consisting of SEQ ID NOs: 1-19, wherein the peptide does not include a full-length protein from which the peptide was derived. In some embodiments, the peptide includes not more than 50, 45, 40, 35, 30, 25 or 20 contiguous amino acid residues of the protein from which the peptide was derived.

In other embodiments, the peptide consists essentially of an amino acid sequence selected from the group consisting of SEQ ID NOs: 1-19.

According to another aspect, a combinatorial peptide is provided that includes an isolated peptide disclosed herein conjugated or fused to a second peptide or polypeptide.

According to another aspect, a composition or article of manufacture is provided that includes one or more of the isolated peptides disclosed herein, or one or more of the combinatorial peptides disclosed herein, and a carrier or excipient. In some embodiments, the carrier or excipient is a pharmaceutically acceptable carrier or excipient. In some embodiments, the one or more of the isolated peptides or one or more of the combinatorial peptides include protease cleavage sites; optionally the protease cleavage sites are different in different peptides or combinatorial peptides. In some embodiments, the one or more isolated peptides or one or more combinatorial peptides are anchored to a scaffold, which optionally is a bioerodible and non-immunogenic scaffold.

According to another aspect, methods are provided to promote wound healing in a subject in need thereof. The methods include administering to the subject an effective amount of one or more of the isolated peptides disclosed herein, one or more of the combinatorial peptides disclosed herein, or the composition or article of manufacture disclosed herein.

In some embodiments, the peptide consists essentially of an amino acid sequence selected from the group consisting of SEQ ID NOs: 1-19. In some embodiments, the peptide is administered in an amount effective to enhance the rate of migration of keratinocytes or endothelial cells, or a combination of keratinocytes and endothelial cells, towards a wound edge. In some embodiments, the administration of the peptide results in an increase in the re-epithelialization of the wound. In some embodiments, the administration of the peptide results in an increase in angiogenesis in or near the wound. In some embodiments, the peptide is administered at a wound site. In some embodiments, the wound is a thermal, chronic, acute or surgical wound.

In some embodiments, the methods further include administering to the subject a second agent. In some embodiments, the second agent is a polypeptide. In some embodiments, the second agent is a growth factor, cytokine, or enzyme. In some embodiments, the second agent is a non-human collagenase. In some embodiments, the non-human collagenase is bacterial collagenase.

In some embodiments, the subject is a mammalian subject. In some embodiments, the mammalian subject is a human.

The various embodiments described herein can be complimentary and can be combined or used together in a manner understood by the skilled person in view of the teachings contained herein. Unless otherwise defined, all technical and scientific terms used herein have the same meaning as commonly understood by one of ordinary skill in the art to which technology provided herein belongs. Although methods and materials similar or equivalent to those described herein can be used in the practice or testing of aspects of the technology provided herein, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and are not intended to be limiting.

Figure 1A:
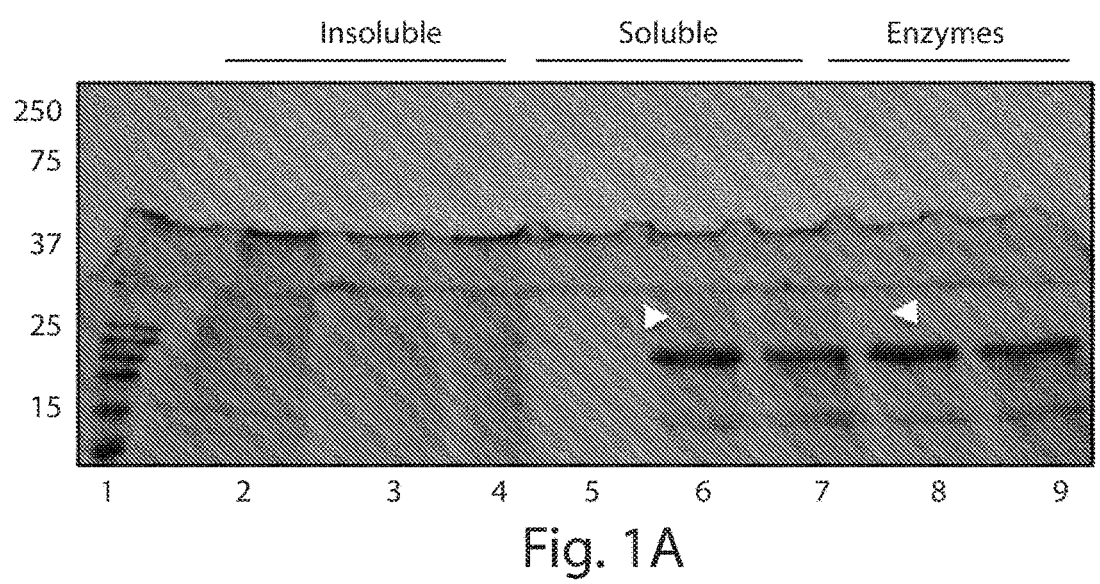
FIGS. 1A-1B show that SANTYL® collagenase API releases unique fragments from human endothelial ECM and matrices derived from human fibroblasts (shown). The matrices were prepared and processed as described in references 5,8-10. Samples derived from buffer insoluble and soluble ECM fractions as well as self-degraded enzymes were loaded into SDS-containing PAGE and subjected to electrophoresis. Unique protein bands present within soluble fractions of digested matrices (arrowheads) were analyzed by mass spectrometry. Identity of the samples in the lanes: 1—Molecular weight standards (kDa); 2—intact ECM; 3, 4—ECM digested with irradiated collagenase for 2 or 24 hours; 5,6—ECM digested with non-irradiated collagenase for 2 or 24 hours; 7,8—ECM digested with irradiated collagenase for 2 or 24 hours; 9, 10—ECM digested with non-irradiated collagenase for 2 or 24 hours. Lanes 2-6—insoluble fraction, lanes 7-10—soluble fraction.

Other objects, features, and advantages of the technology provided herein will become apparent from the following detailed description. It should be understood, however, that the detailed description and the specific examples, while indicating preferred embodiments of the technology provided herein, are given by way of illustration only, since various changes and modifications within the spirit and scope of the technology provided herein will become apparent to those skilled in the art from this detailed description.

DETAILED DESCRIPTION

Wound healing is predicated upon the migration and proliferation of cells at or near the wound edge and the recruitment of new or pre-existing blood vessels to the wound site. Provided herein are wound healing peptides that stimulate keratinocyte and/or endothelial cell motility and/or proliferation. Also provided herein are kits and articles of manufacture comprising one or more of the wound healing peptides.

Wound Healing Peptides and Encoding Wound Healing Peptide Nucleic Acids

As described herein, treatment of extracellular matrices (ECM) with the active pharmaceutical ingredient (API) in SANTYL® collagenase Ointment, a bacterial collagenase isolated from a Clostridial bacterium results in the liberation of several peptides not known to be found as such in nature. These peptides are believed not formed by the treatment of ECM with a human collagenase. These peptides can be isolated from digested ECM, produced in cells by expression of recombinant nucleic acids encoding the peptide(s), or synthesized using conventional peptide synthesis methods well-known in the art. Further, combinatorial peptides can be generated by combining all or portions of two or more wound healing peptides. Exemplary peptides and combinatorial peptides (SEQ ID NOs: 1-19) are provided in Table 1.

The methods, kits, and articles of manufacture provided herein can include more than one peptide, wherein at least one of the peptides is selected from SEQ ID NOs: 1-19, or peptides that comprise or consist essentially of SEQ ID NOs: 1-19.

In some embodiments, a wound healing peptide includes an amino acid sequence selected from the group consisting of SEQ ID NOs: 1-19, and the peptide comprises 100, 95, 90, 85, 80 75, 70, 65, 60, 55, 50, 45, 40, 35, 30, 25, 20, or fewer amino acids. Thus a wound healing peptide can comprise 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 amino acids.

In other embodiments, a wound healing peptide includes an amino acid sequence selected from the group consisting of SEQ ID NOs: 1-19, and the peptide does not comprise a full-length protein from which the peptide was derived. In some of such embodiments, the peptide comprises not more than 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9 or 8 contiguous amino acid residues of the protein from which the peptide was derived.

Certain wound healing peptides are combinatorial peptides which are combinations of peptides that include at least one of the peptides disclosed herein. Such peptides are not naturally occurring and cannot be produced by in situ cleavage. Instead, combinatorial peptides are produced by chemical synthesis or by expression of a recombinant nucleic acid that encodes the combinatorial peptide, such as a protein expression vector as described elsewhere herein. Non-limiting examples of combinatorial peptides include peptides that comprise one or more of SEQ ID NOs: 1-8, 11, 12, 14-17. For example, of the peptides disclosed herein, peptides TSN9, TSN10, TSN13, TSN18 and TSN19 (SEQ ID NOs: 9, 10, 13, 18 and 19) are examples of combinatorial peptides; see Table 1.

In some embodiments, the peptides can be linked consecutively, with the C-terminal end of one peptide linked via peptide bond to the N-terminal amino acid of another peptide. In other embodiments, the peptides are linked by one or more linkers that can include one or more amino acids that are not part of the peptides linked in the combinatorial peptide.

The wound-healing properties of the disclosed wound healing peptides have been demonstrated herein, using well characterized in vitro and in vivo methods and wound healing assays. The results of the assays are described herein. The wound healing peptides provided herein are also useful in the promotion of capillary morphogenesis and to induce endothelial cell proliferation. Cells types that can be affected by the wound healing peptides provided herein include keratinocytes, endothelial cells such as microvascular endothelial cells, fibroblasts and pericytes.

The wound healing peptides provided herein also can be used in conjunction with a bio-compatible wound product. As described herein, the wound product can be, for example, a biomaterial derived from mammalian tissue. The wound product can be provided in purified or unpurified form. In addition, the wound product can be modified by the addition of one or more compounds that act as functional crosslinkers (e.g., 1-Ethyl-3-[3-dimethylaminopropyl]carbodiimide hydrochloride (EDC) or N-hydroxysulfosuccinimide (sulfo-NHS)). For example, a commercially-available wound product (e.g., OASIS® Wound Matrix, distributed by Smith & Nephew, Fort Worth, Tex.) can be combined with a wound healing peptide, in the presence or absence of one or more functional crosslinkers. As described herein, peptides can be engineered to possess cleavage sites so that they can be quantitatively released, unhindered or without loss of bioactivity, from the scaffold to act in a temporally and spatially specific manner. For example, anchoring on a scaffold would afford release of an angiogenically-active bioactive peptide before the controlled release of a bioactive peptide that promotes epithelialization. In this way, blood vessel formation would be activated before epithelialization so that nutrients could be locally delivered in support of the epithelialization process by the angiogenic peptide activators preceding the epithelialization activators.

Also provided herein are nucleic acid molecules that encode the disclosed wound healing peptides and combinatorial peptides. The sequence of such nucleic acids is determined according to the standard genetic code in which one or more three-nucleotide codons encode an amino acid of the wound healing peptides or combinatorial peptides.

Kits, Articles of Manufacture, and Absorbent Products

Provided herein are kits for the treatment of wounds in a subject, containing one or more wound healing peptides. In some embodiments, the kit includes instructions for using the peptide to treat a wound or wounds in the subject. In some embodiments, the kit includes one or more other materials that enhance wound healing. For example, the kit can contain a bio-compatible wound product, a growth factor, a cytokine, or an enzyme. Suitable subjects, include, for example, a patient with having a wound. In some embodiments, the patient has diabetes. In other embodiments, the subject is a burn patient. In some embodiments, the wound is a chronic wound. A non-human (e.g., bacterial) collagenase may also be included in the kit.

Articles of manufacture are also provided. For example, an article of manufacture includes one or more wound healing peptides (e.g., one or more peptides including the amino acid sequence of any one or more of SEQ ID NOs: 1-19) and, optionally, one or more growth factors, cytokines, or enzymes. The article is suitable for use in a medical treatment of a mammalian subject. For example, the article can be or include a skin or tissue equivalent. In some embodiments, the article comprises one or more growth factors, cytokines, or enzymes. A non-human (e.g., bacterial) collagenase may also be included in or on the article.

Provided herein are absorbent products. Suitable absorbent products, for example, are capable of absorbing a wound fluid when applied at a wound site. In some embodiments, the absorbent product comprises a structure that is capable of absorbing liquid and a wound healing peptide. Exemplary structures include, for example, bandages, gauzes, wound or sore dressings, dermal patches and adhesive tapes. The term "liquid absorbent structure" refers broadly to any material applied to a wound for protection, absorbance, drainage, etc. Thus, adsorbent and absorbent materials are specifically contemplated as a solid support. Numerous types of dressings are commercially available, including films (e.g., polyurethane films), hydrocolloids (hydrophilic colloidal particles bound to polyurethane foam), hydrogels (cross-linked polymers containing about at least 60% water), foams (hydrophilic or hydrophobic), calcium alginates (nonwoven composites of fibers from calcium alginate), and cellophane (cellulose with a plasticizer). Specifically contemplated is the use of liquid absorbent structures where one or more wound healing peptides are impregnated within or attached (covalently or otherwise) to the surface of the structure.

Wound Healing Peptide Synthesis, Expression and Purification

Wound healing peptides described herein can be produced synthetically, or by proteolytic digestion of suitable biological materials by one or more enzymes such as collagenase. Alternatively, nucleotide sequences encoding wound healing peptides can be introduced into a protein expression vector and produced in a suitable host organism (e.g., bacteria, yeast, insect cells, etc.). Regardless of the origin or method of producing the peptides, following production, the peptides can be isolated and optionally purified. Peptides can be engineered to possess known wound protease cleavage sites to release a bioactive wound healing peptide or an angiogenesis-activating peptide locally with time and space control.

Modified Wound Healing Peptides

The wound healing peptides provided herein can be modified as is well-known in the art. For example, the wound healing peptides are modified by the addition of one or more functional groups such as phosphate, acetate, or various lipids and carbohydrates. Wound healing peptides can also exist as peptide derivatives. The term "peptide derivative" refers to compound having an imino group (—NH—), and more particularly, a peptide bond. Peptides may be regarded as substituted amides. Like the amide group, the peptide bond shows a high degree of resonance stabilization. The C—N single bond in the peptide linkage has typically about 40 percent double-bond character and the C=O double bond about 40 percent single-bond character. "Protecting groups" are those groups that prevent undesirable reactions (such as proteolysis) involving unprotected functional groups. In one embodiment, the protecting group is an acyl or an amide. In one embodiment, the acyl is acetate. In another embodiment, the protecting group is a benzyl group. In another embodiment, the protecting group is a benzoyl group. The technology provided herein includes combinations of such protecting groups.

"Peptide" or "polypeptide" refers to a polymer in which the monomers are alpha amino acids joined together through amide bonds. Peptides are two or often more amino acid monomers long. The term "dimer" as in a "peptide dimer" refers to a compound in which two peptide chains are linked; generally, although not necessarily, the two peptide chains will be identical and are linked through a linking moiety covalently bound to the carboxyl terminus of each chain. Amino acid residues in peptides are abbreviated as follows: Phenylalanine is Phe or F; Leucine is Leu or L; Isoleucine is Ile or I; Methionine is Met or M; Valine is Val or V; Serine is Ser or S; Proline is Pro or P; Threonine is Thr or T; Alanine is Ala or A; Tyrosine is Tyr or Y; Histidine is His or H; Glutamine is Gin or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; and Glycine is Gly or G. Stereoisomers (e.g., D-amino acids) of the twenty conventional amino acids, unnatural amino acids such as a,a-disubstituted amino acids, N-alkyl amino acids, lactic acid, and other unconventional amino acids may also be suitable components for compounds of the technology provided herein. Examples of unconventional amino acids include: .beta.-alanine, 1-naphthylalanine, 2-naphthylalanine, 3-pyridylalanine, 4-hydroxyproline, 0-phosphoserine, N-acetylserine, N-formylmethionine, 3-methylhistidine, 5-hydroxylysine, norleucine, and other similar amino acids and imino acids (e.g., 4-hydroxyproline).

An additional polypeptide ("tag") can be added on for the purpose of purifying or identifying or purifying the wound healing peptides. Protein tags make it possible, for example, for the polypeptides to be adsorbed, with high affinity, to a matrix, and for the matrix then to be washed stringently with suitable buffers without the complex being eluted to any significant extent, and for the adsorbed complex subsequently to be eluted selectively. Examples of the protein tags which are known to the skilled person are a (His)6 tag, a Myc tag, a FLAG tag, a haemagglutinin tag, a glutathione transferase (GST) tag, an intein having an affinity chitin-binding tag or maltose-binding protein (MBP) tag. These protein tags can be located N-terminally, C-terminally and/or internally in or to the peptide sequence.

Methods of Use and Treatment

Also provided herein are methods for the treatment of wounds using wound healing peptides in combination with other biological materials that promote or augment wound healing responses. Such biological materials include, without being limited to, growth factors, cytokines, enzymes, and ECM components. For example, collagenase treatment of the sub-endothelial extracellular matrix can be used in combination with wound healing peptide treatment to accelerates endothelial migration and proliferation to a level greater than the inductive influence of collagenase treatment in the absence of wound healing peptides.

The wound healing peptides are administered orally, topically, or by parenteral means, including subcutaneous and intramuscular injection, implantation of sustained release depots, intravenous injection, intranasal administration, and the like. The wound healing peptides are administered in an amount or dose that is pharmaceutically or therapeutically effective. A pharmaceutically or therapeutically effective dose or amount refers to a dose or amount of wound healing peptides or a composition containing wound healing peptides sufficient to induce a desired biological result. That result can be alleviation of the signs, symptoms, or causes of a disease, or any other desired alteration of a biological system. Preferably, this dose or amount will be sufficient to stimulate or augment the epithelial and/or endothelial wound healing response and, thus, induce or potentiate wound healing.

Compositions and Pharmaceutical Compositions

The wound healing peptides disclosed herein are provided in a variety of compositions compatible with peptides, as are known in the art. Such compositions can include one or more wound healing peptides, and one or more carriers or excipients. Wound healing peptides may be administered as a pharmaceutical composition comprising one or more wound healing peptides in combination with one or more pharmaceutically acceptable carriers or excipients. Such compositions may be aqueous solutions, emulsions, creams, ointments, suspensions, gels, liposomal suspensions, and the like. Suitable carriers (excipients) include water, saline, Ringer's solution, dextrose solution, and solutions of ethanol, glucose, sucrose, dextran, mannose, mannitol, sorbitol, polyethylene glycol (PEG), phosphate, acetate, gelatin, collagen, CARBOPOL®, vegetable oils, and the like. One may additionally include suitable preservatives, stabilizers, antioxidants, antimicrobials, and buffering agents, for example, BHA, BHT, citric acid, ascorbic acid, tetracycline, and the like. Cream or ointment bases useful in formulation include lanolin, SILVADENE®, AQUAPHOR®, and the like. Other topical formulations include aerosols, bandages and other wound dressings. Alternatively one may incorporate or encapsulate the wound healing peptides in a suitable polymer matrix or membrane, thus providing a sustained-release delivery device suitable for implantation near the site to be treated locally. Other suitable devices for delivering or administering the compositions provided herein include indwelling catheters and devices such as the ALZET® minipump. Ophthalmic preparations may be formulated using commercially available vehicles such as SORBICARE®, NEODECADRON®, LACRILUBE®, and the like or may employ topical preparations such as that described in U.S. Pat. No. 5,124,155, incorporated herein by reference.

"Pharmaceutically acceptable salts" refer to the non-toxic alkali metal, alkaline earth metal, and ammonium salts commonly used in the pharmaceutical industry including the sodium, potassium, lithium, calcium, magnesium, barium, ammonium and protamine zinc salts, which are prepared by methods well known in the art. The term also includes non-toxic acid addition salts, which are generally prepared by reacting the compounds provided herein with a suitable organic or inorganic acid. Representative salts include the hydrochloride, hydrobromide, sulfate, bisulfate, acetate, oxalate, valerate, oleate, laurate, borate, benzoate, lactate, phosphate, tosylate, citrate, maleate, fumarate, succinate, tartrate, napsylate and the like.

The term "pharmaceutically acceptable" refers to compounds and compositions which may be administered to mammals without undue toxicity. Exemplary pharmaceutically acceptable salts include mineral acid salts such as hydrochlorides, hydrobromides, phosphates, sulfates, and the like; and the salts of organic acids such as acetates, propionates, malonates, benzoates, and the like.

Further, one or more wound healing peptides may be provided in a heat stable form, such as in a powdered or encapsulated formulation for delivery and use without the need for refrigeration. Examples of such forms include solid forms, especially as a lyophilized powder. Lyophilized formulations typically contain stabilizing and bulking agents, for example human serum albumin, sucrose, mannitol, and the like. A thorough discussion of pharmaceutically acceptable excipients is available in Remington's Pharmaceutical Sciences (17th edition, Mack Publishing Co., Easton, Pa.).

The technology provided herein is not limited to the particular methodologies, protocols, constructs, formulae and reagents described but further include those known to the skilled artisan. It is also to be understood that the terminology used herein is for the purpose of describing particular embodiments only, and is not intended to limit the scope of the technology provided herein.

Unless defined otherwise, all technical and scientific terms used herein have the same meaning as commonly understood to one of ordinary skill in the art to which technology provided herein belongs. Any methods, materials, and kits similar or equivalent to those described herein can be used in the practice or testing of the technology provided herein.

EXAMPLES

The invention now being generally described, it will be more readily understood by reference to the following examples, which are included merely for purposes of illustration of certain embodiments and embodiments of the present invention, and are not intended to limit the invention.

Example 1

Biochemical Characterization of SANTYL® Collagenase API and its Extracellular Matrix-Derived Peptide Producing Activities: Identification and Creation of Innovative, Bioactive ECM-Derived Wound Healing Peptides The active pharmaceutical ingredient (API) enzyme(s) present within SANTYL® collagenase Ointment were used to produce peptides from well-defined, bio-synthesized extracellular matrices derived from living, human epidermal and dermal cell cultures in vitro. Limited collagenase-dependent ECM digestions were followed by polyacrylamide gel electrophoresis and mass spectrometry. SANTYL® collagenase API-mediated ECM degradation of human capillary and dermally-derived endothelium- and human dermal fibroblast-derived matrices leads to release of several unique fragments.

Fifteen collagenous and collagen-associated ECM peptides, of 8-21 amino acids in length, have now identified, sequenced and synthesized. Mass spectrometric identification of releasates reveals a cell type-specific array of peptides including key peptides derived from the extracellular matrix-bound and collagen-associated macromolecules (i) thrombospondin, (ii) multimerin and (iii) fibronectin, which are collagenase-sensitive and released from endothelial ECM. In addition, collagenase yields peptides from (i) TGF-β-induced protein and (ii) collagen VI, which are derived from ECM synthesized and organized by human dermal fibroblasts. Peptides have been synthesized from these original structures bearing hydrophobicity and hydrophilicity profiles, which insures that each peptide is soluble in water.

Figure 1B:
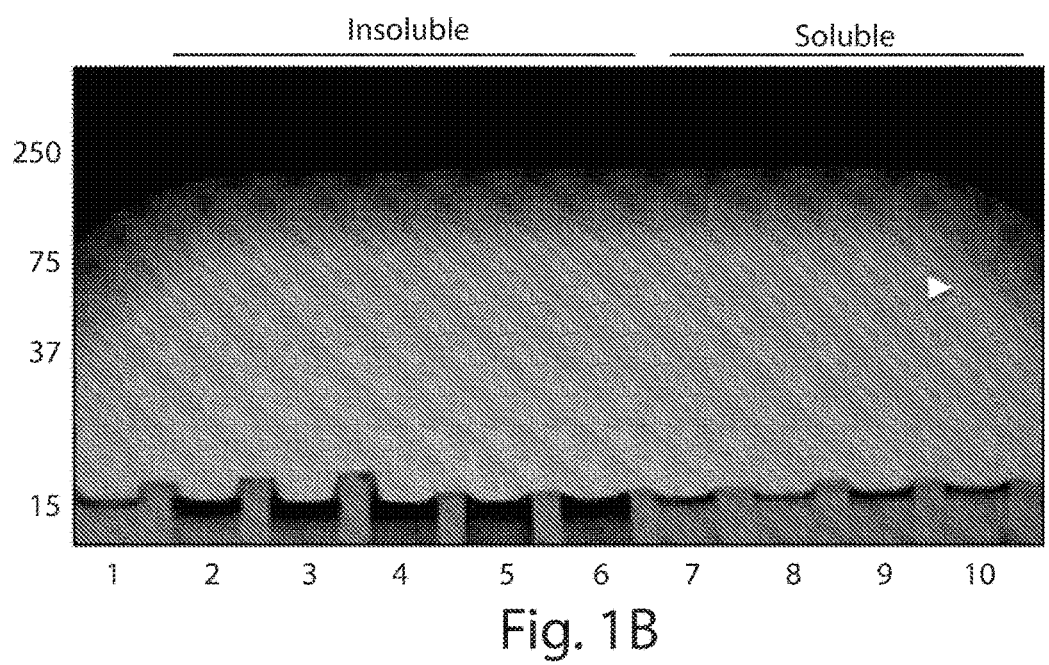

In addition to these peptides, which were produced by collagenase cleavage of synthesized endothelial or fibroblastic matrices, four peptides were "re-engineered". These re-engineered peptides are not naturally produced via collagenase-digestion; the collagenase-produced "parent" peptide(s) were re-engineered to optimize and maximize wound healing potential. These include peptides TSN9, TSN10, TSN18, TSN19, which possess amino acid sequence identity to, at least, two distinct collagenase-liberated peptides identified by mass spectrometry (see FIG. 1, Table 1). The peptides were synthesized at Tufts University Core Facility and their biological activity evaluated in a series of tests, including (i) ability to stimulate cell-specific proliferation, (ii) activation of angiogenesis and (iii) wound healing, in vitro and in vivo.

TSN Peptides 1-9 are derived from Human Dermal Endothelial Cell Extracellular Matrix. TSN Peptides 10-19 are derived from Human Dermal Fibroblast Extracellular Matrix). The procedure for producing extracellular matrix is from Herman and Castellot, Arteriosclerosis. 1987 September-October; 7(5):463-9.

TABLE 1

SANTYL® collagenase API-produced and Extracellular Matrix-derived Peptides

| Peptide Name | Peptide Length | Peptide Sequence (NH$_2$→COOH) | SEQ ID NO | Origin |
|---|---|---|---|---|
| TSN1 | 14 aa | NFQGVQNRFVFGTP | 1 | Thrombospondin-1 Laminin G-like domain |
| TSN2 | 16 aa | MENAELDVPIQSVFTR | 2 | Thrombospondin-1 N-terminal domain |
| TSN3 | 11 aa | NTDNIYPESSC | 3 | Multimerin EGF-liked domain |
| TSN4 | 8 aa | PYLGYVFK | 4 | Multimerin C1q domain |
| TSN5 | 18 aa | MQTVAQLFKTVSSLSLST | 5 | Multimerin-1 Coiled coil domain |
| TSN6 | 19 aa | HSPDIQLQKGLTFEPIQIK | 6 | Multimerin-1 Coiled coil domain |
| TSN7 | 16 aa | STITQPYKTLNNARSP | 7 | Fibronectin Heparin-binding domain |
| TSN8 | 16 aa | RPGPSPEGTGQSYNYR | 8 | Fibronectin Fibrin-binding 2 domain |
| TSN9 | 16 aa | MENAELDPPYLGYVFK | 9 | Combination of Thrombospondin and multimerin peptides |
| TSN1020 | aa | TGQSYNQYSQRPYLGVYVFK | 10 | Combination of Thrombospondin and multimerin peptides |
| TSN1110 | aa | LYGQTPLETL | 11 | TGF-β-induced protein: Fas1/3 domain |
| TSN1211 | aa | ELADSPALEIG | 12 | TGF-β-induced protein: N-terminal domain |
| TSN1321 | aa | LYGQTPLETLELADSPALEIG | 13 | Combination of 11 and 12 |
| TSN1414 | aa | VSGNTVEYALPTLE | 14 | Tenascin C Fibronectin Type III domain 14 |
| TSN1518 | aa | LDSPTAPTVQSTALTWRP | 15 | Tenascin C Fibronectin III domain 15 |
| TSN1617 | aa | LDGSAPGPLYTGSALDF | 16 | Collagen (VI) Alpha-3 VWFA domain 3 |
| TSN1711 | aa | GSEGVRSGRSG | 17 | Collagen (VI) Alpha-3 VWFA domain 6 |
| TSN1814 | aa | QPQPLPSPGVGGKN | 18 | Combination of non-helical Collagen (VI) Alpha-3 chain regions |
| TSN1911 | aa | KYTLNPVIDAS | 19 | Combination of fibronectin Type-III 14 domain of fibronectin |

Example 2

SANTYL® Collagenase API-Produced and Extracellular Matrix-Derived Peptides Significantly Stimulate the Cellular Responses to Injury In Vitro Cell Proliferation, Post-Injury Migration and Angiogenesis.

Figure 2:
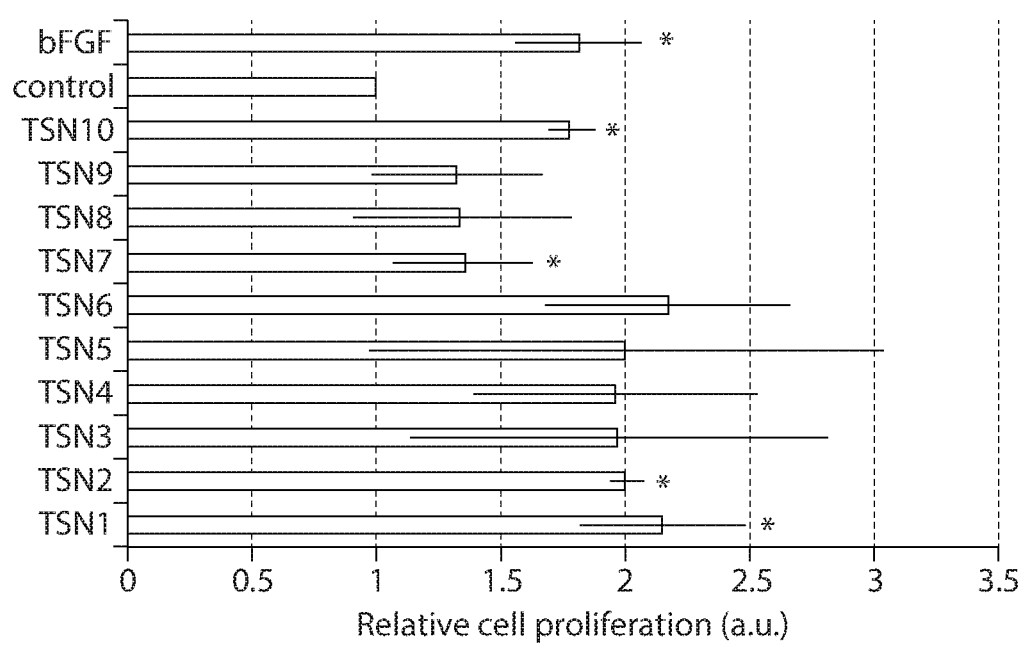
FIG. 2 shows that peptides derived from human endothelial ECM stimulate proliferation of human endothelial cells. Human microvascular endothelial cells were plated at low density in multi-well plates and treated with 100 nM peptides every other day. At day 5 post-plating the cells were counted using a coulter counter. Cell proliferation relative to control is shown. *statistical significance ($p<0.05$).
Figure 3A:
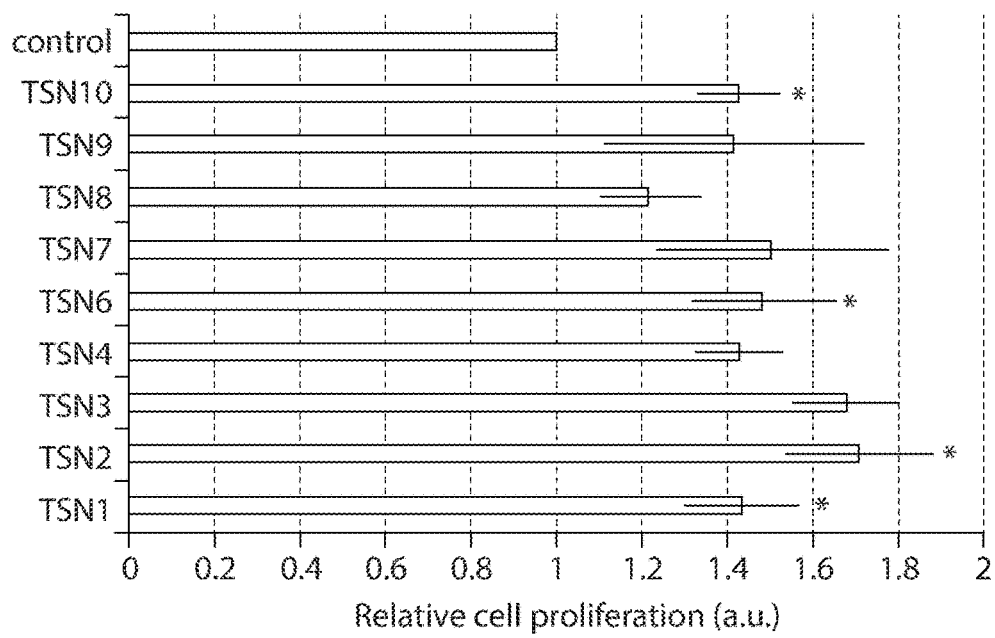
FIGS. 3A-3B show that peptides derived from human endothelial ECM stimulate proliferation of adult human keratinocytes in dose-dependent manner. Adult human keratinocytes were plated at low density in multi-well plates and treated with 10 nM peptides (FIG. 3A) or 1-100 nM peptides (FIG. 3B) every other day. At day 7 post-plating the cells were counted using a coulter counter. Cell proliferation relative to control (FIG. 3A) or absolute cell number grown (FIG. 3B) are shown. *statistical significance ($p<0.05$).
Figure 3B:
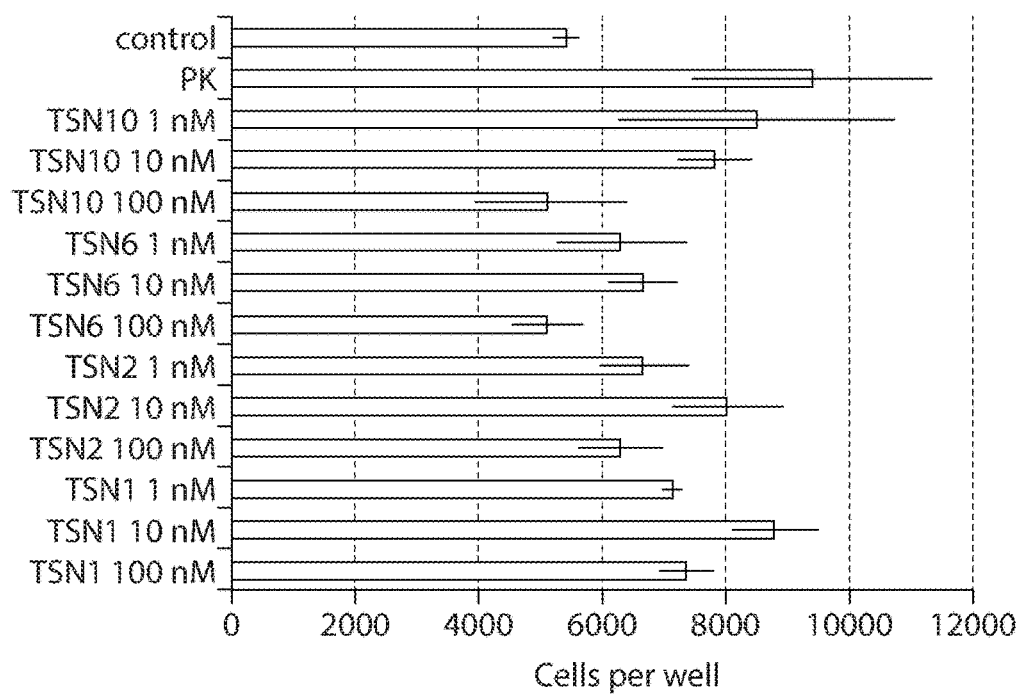

In our efforts aimed at characterizing the growth-promoting, migration-enhancing and angiogenesis-inducing activities embodied in SANTYL® collagenase Ointment and in an effort focused on contrasting the efficacy of collagenase vs. the newly-discovered SANTYL® collagenase API-derived bioactive wound healing peptide(s), we continue to perform a battery of pre-clinical tests and trials using the well-established models of injury and repair developed, here, at Tufts University School of Medicine and the Center for Innovations in Wound Healing Research. To these ends, we took advantage of the 2D and 3D injury/repair models developed to quantify cellular responses to injury. Outcomes of these studies have conclusively revealed that the newly-discovered peptides are able to promote cellular wound healing responses. As shown in FIG. 2, several TSN peptides possess profound pro-proliferative properties when delivered to human cell cultures, including keratinocytes, endothelial cells and fibroblasts. FIG. 2 shows that TSN1 and TSN2, as representative examples amongst other newly-identified and synthesized ECM-derived peptides, stimulate human dermally-derived microvascular endothelial cell growth in vitro. Indeed, TSN1 and TSN2 exceed the growth-promoting activity embodied in fibroblast growth factor 2 (FGF2), which is, perhaps, amongst the most mitogenic and angiogenesis inducer activities known. Furthermore these bioactive peptides promote adult human keratinocyte proliferation in the 1-10 nM range, e.g. see FIG. 3B, completely accounting for the keratinocyte growth-promoting activity present within PK SANTYL collagenase API (cf. FIG. 3B, PK vs. TSN1, TSN2, TSN10). This is especially noteworthy since these peptides not only promote vascular endothelial growth but, adult human keratinocyte growth.

Figure 4:
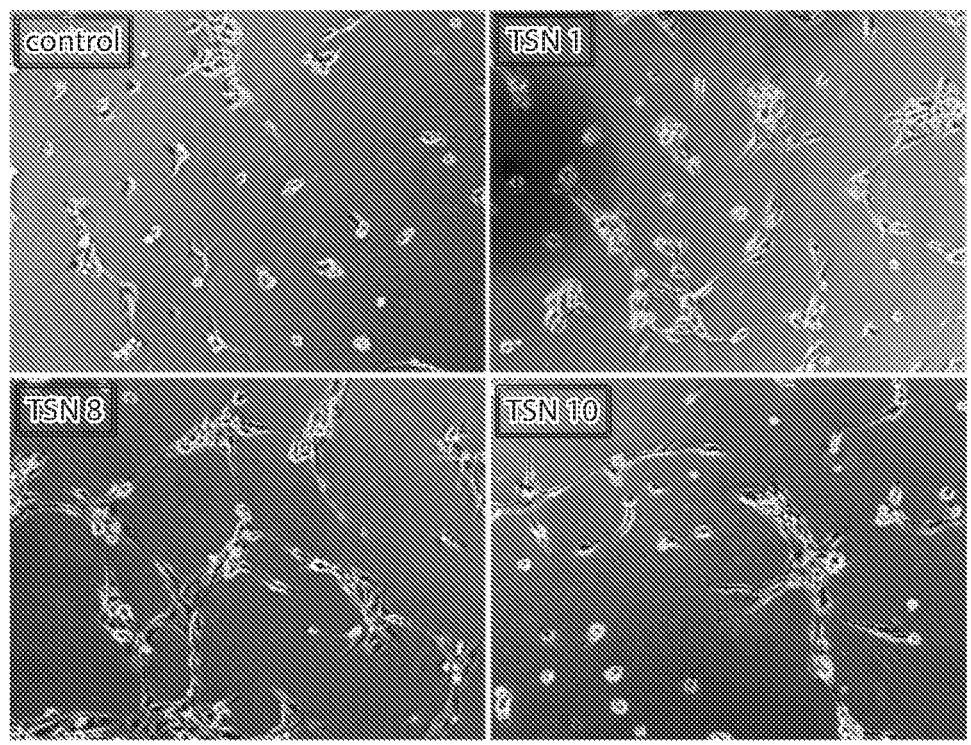
FIG. 4 shows that peptides derived from ECM degraded by bacterial collagenase stimulate angiogenesis in vitro. ECM-derived peptides were dissolved in growth factor-reduced Matrigel at 100 nM, the matrix was allowed to polymerize, human microvascular endothelial cells were plated either in control low serum containing media or media containing 100 nM peptides. Representative images of cells treated with endothelial ECM-derived peptides are shown.

As has been demonstrated in the literature, patent microvascular endothelial lined "tubes" can be produced in vitro when cells are either plated upon or are embedded within growth factor-reduced Matrigel. To ascertain whether the newly-identified and synthesized ECM-derived and "re-engineered" peptides are able to stimulate wound healing angiogenesis, in addition to the microvascular endothelial growth promoting activity already demonstrated, population density matched cell numbers were plated in control or peptide-treated cultures and the angiogenic activities of the peptides quantified as a function of time in culture. As can be seen in a representative example (FIG. 4), when several of the vascular endothelial extracellular matrix-derived peptides were applied to human microvascular endothelial cells isolated from dermal capillaries, there was a marked and significant morphogenetic event, which gives rise to angiogenic activation and tube formation in vitro (FIG. 4). Unlike the control or cell population tested, which was unable to present capillary-like and tube-like arrays, TSN1, TSN8 and TSN10 markedly promoted in vitro angiogenesis. Function-specific domains present within TSN1/2 and the newly-engineered "combinatorial" peptides present within TSN 10 are able to promote in vitro angiogenesis. TSN peptides promote morphogenesis and angiogenic activation by stimulating migration, proliferation and tube formation; peptide-stimulated endothelial tubes are more numerous, of greater length, having more branch points then control treated endothelial cell cultures.

Figure 5:
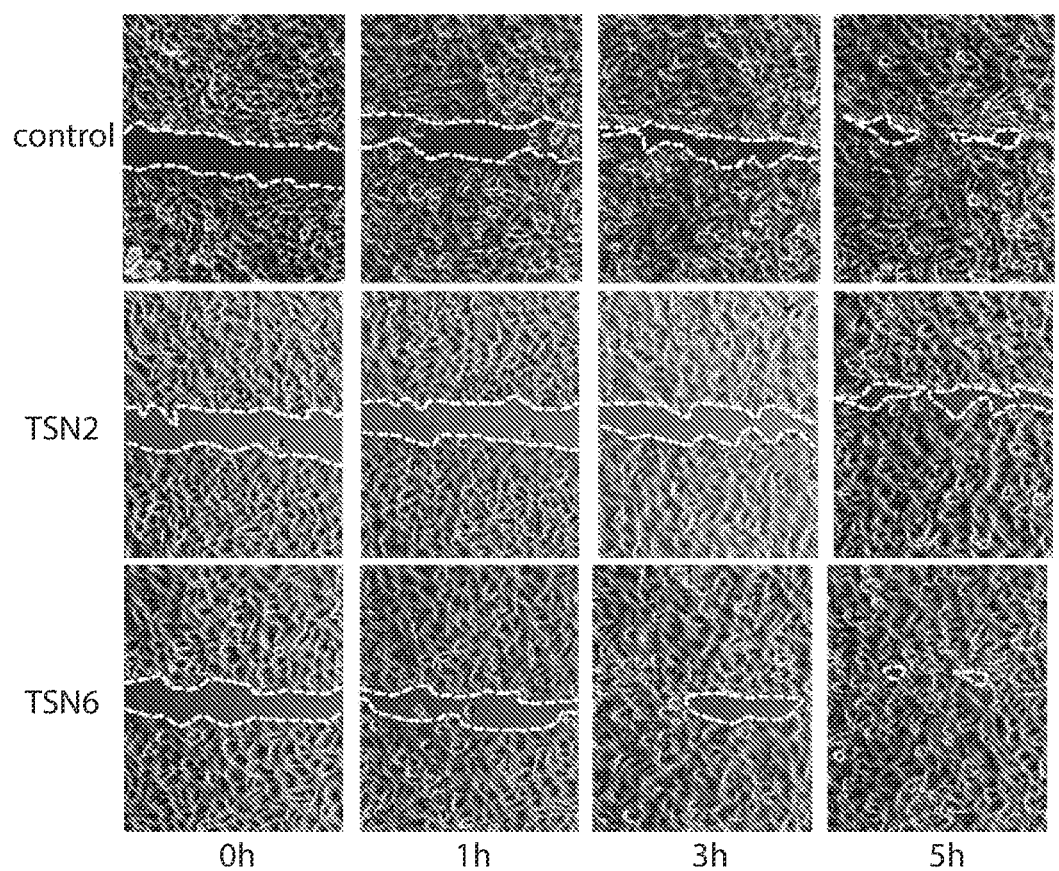
FIG. 5 shows that ECM-derived peptides stimulate epithelial wound healing in vitro. Adult human keratinocytes were plated into glass-bottom well plates at high density. Scratch wounds were made in the cell monolayer 24 h post-plating. The peptides dissolved in keratinocyte growth media (10 nM) were applied immediately after wounding. Wound closure was monitored at 0, 1, 3 and 5 hours post-injury. Dashed line outlines the wounds. Representative images of wounds treated with TSN2 and TSN6 are shown.

To determine whether post-injury migration is similarly stimulated, a series of studies were performed to demonstrate whether or to what extent one or another of the bioactive peptides could promote the migratory response to injury. Human epidermis-derived keratinocytes were plated at a post-confluent density prior to mechanical injury in the presence or absence of bioactive wound healing peptides or control entities. FIG. 5 demonstrates the marked migration-enhancing activity embodied within the peptides, including TSN 2 and TSN 6. Similarly, since TSN2, which has angiogenesis-inducing activity also promotes keratinocyte migration in response to injury, these data suggest that the migration-enhancing activity embodied in this thrombospondin-1 domain may act upon keratinocytes and endothelial cells in the same manner or through the same molecular mechanism(s).

Example 3

SANTYL® Collagenase API-Produced and Extracellular Matrix-Derived Peptides Significantly Stimulate the Cellular Responses to Injury and Wound Healing in Vivo The peptides described herein, which have significant migration-enhancing, growth-promoting and angiogenesis-inducing activity in vitro, similarly possess wound healing activity in vivo. For the wound healing studies in vivo, a model of impaired healing, cyclophosphamide-induced neutropenia, was used. Full thickness excisional wounding of the cutaneous tissues located over the cranium was performed. While only one 8 mm diameter full thickness excisional wound can be made per mouse, the means by which healing occurs is closely aligned with human cutaneous wound healing, i.e., via migration and proliferation vs. contraction (as is the case on the rodents' flanks). To these ends, animals were treated according to NIH guidelines for the care and well-being of laboratory animals, were injured under full anesthesia and then receive pain-alleviation, post-operatively.

Following cyclophosphamide treatment, animals were injured and then wounds treated/covered. Test entities were coded so that the nature of the experiment was blinded to the investigator; and, each specimen was evaluated and scored blindly according to the wound healing system shown in Table 2, prior to unmasking the experimental code. To date, several experiments have been performed where each test entity is delivered in quadruplicate; dosing studies are in progress using doses of the peptides in the nanomolar (nM) to micromolar (µM) range.

TABLE 2

Figure 6:
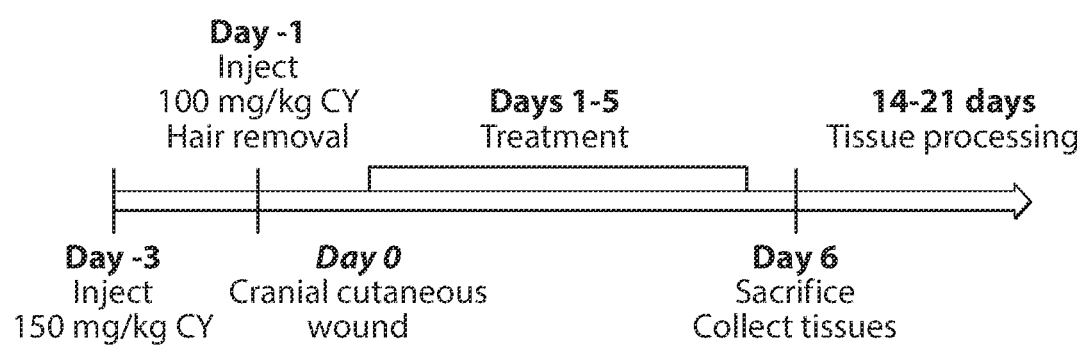
FIG. 6 shows the experimental design for in vivo testing of peptides. Balb/c mice were pre-treated with cyclophosphamide at 150 mg/kg 3 days prior to injury and with 100 mg/kg cyclophosphamide 1 day before injury. Cranial cutaneous wounds were created using 4 mm punch biopsy tool and immediately covered with adherent transparent dressing (TEGADERM™). The peptides were prepared fresh daily and injected under the dressing on days 1-5 post injury. On day 6 after wounding the animals were sacrificed according to Division of Laboratory Animal Medicine (DLAM) approved procedures. Wounds together with surrounding healthy tissues were excised, cut in half along the midline and either fixed in 4% phosphate buffered formaldehyde or frozen in OCT for further processing.
Figure 7A:
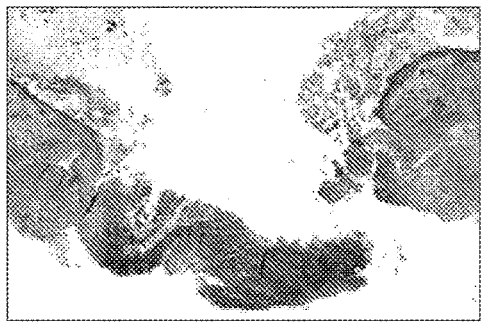
FIGS. 7A-7L show that ECM-derived peptides stimulate cellular responses to injury in a mouse model of impaired healing. Cranial cutaneous wounds were created in cyclophosphamide-treated mice as previously described (reference 5). Peptides dissolved in carboxymethyl cellulose (CMC) (1 mg/ml) were applied daily. Mice were sacrificed at day 6 post-injury. Wounds were excised, formalin-fixed, paraffin embedded, cut and stained with haematoxylin and eosin. Representative images of wounds treated with CMC (A, B), irradiated bacterial collagenase (C, D), TSN6 at 0.1 mg/ml (E, F), TSN6 at 1 mg/ml (G, H), TSN18 at 0.1 mg/ml (I, J) or TSN18 at 1 mg/ml (K, L). Scale bar 1 mm.
Figure 7B:
Figure 7C:
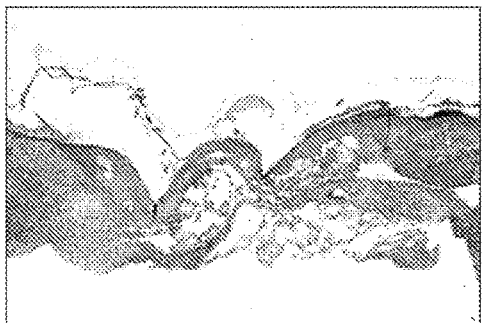
Figure 7D:
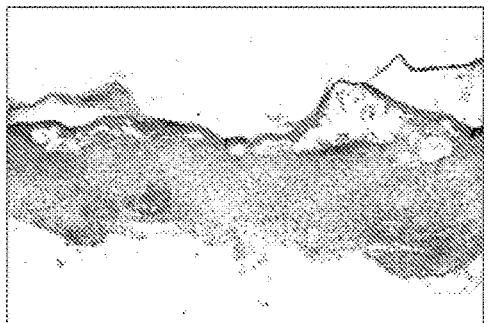
Figure 7E:
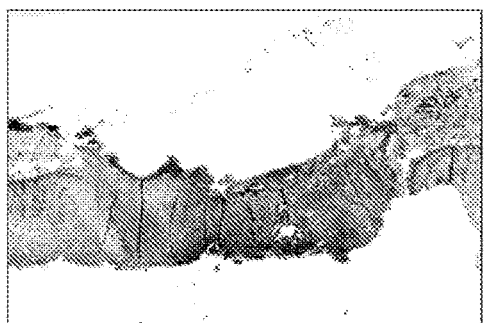
Figure 7F:
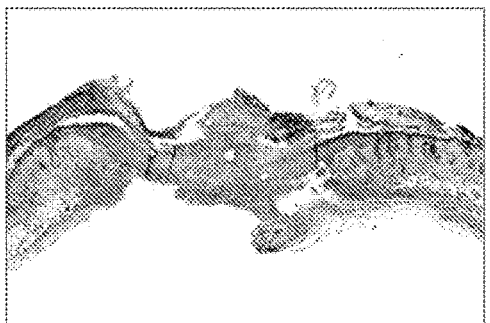
Figure 7G:
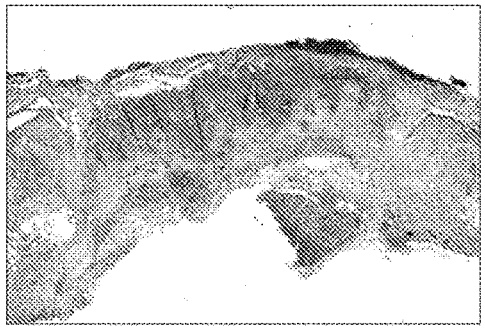
Figure 7H:
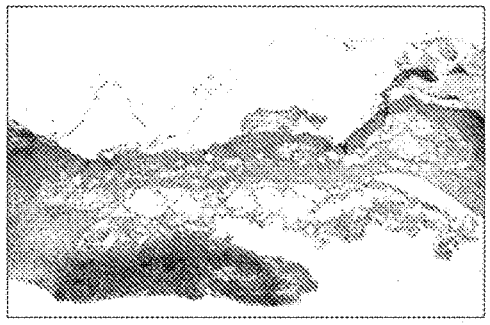
Figure 7I:
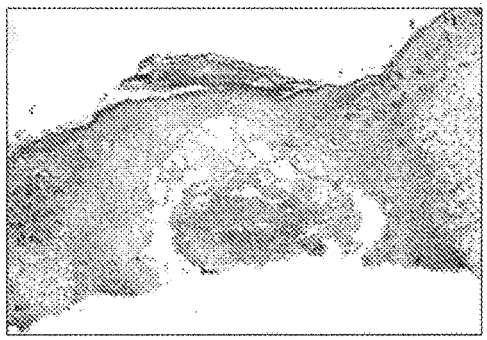
Figure 7J:
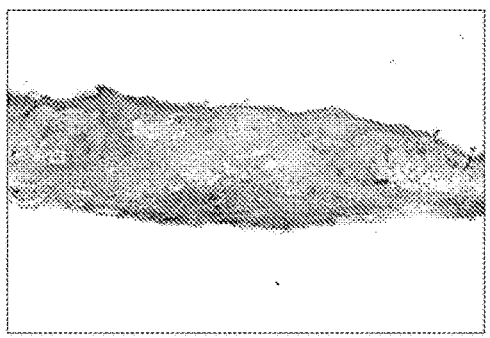
Figure 7K:
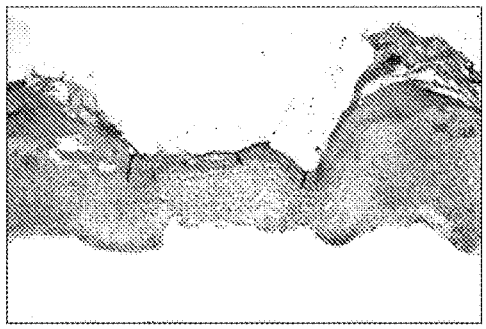
Figure 7L:
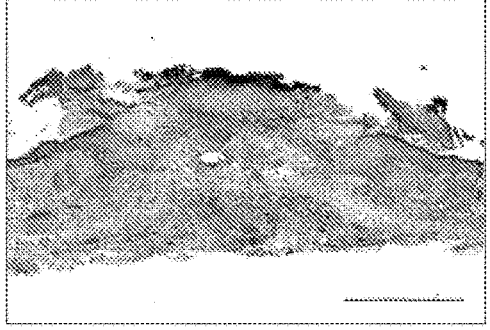
Figure 8:
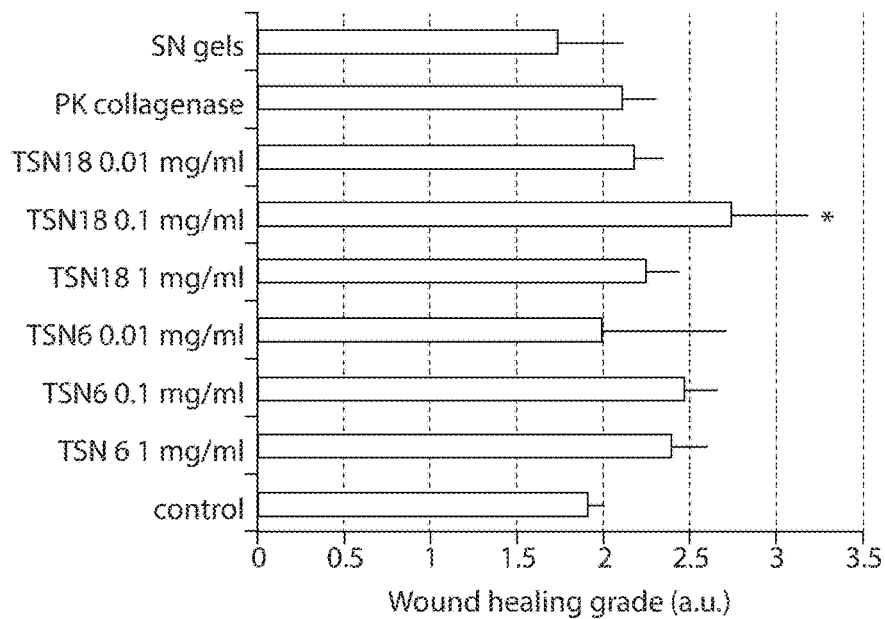
FIG. 8 shows that ECM-derived peptides stimulate wound healing in mice. Wounds were created, treated as described in FIG. 6 and scored in a blind manner according to the grading described in Table 2. * indicates statistical significance of findings ($p<0.05$).
Figure 9:
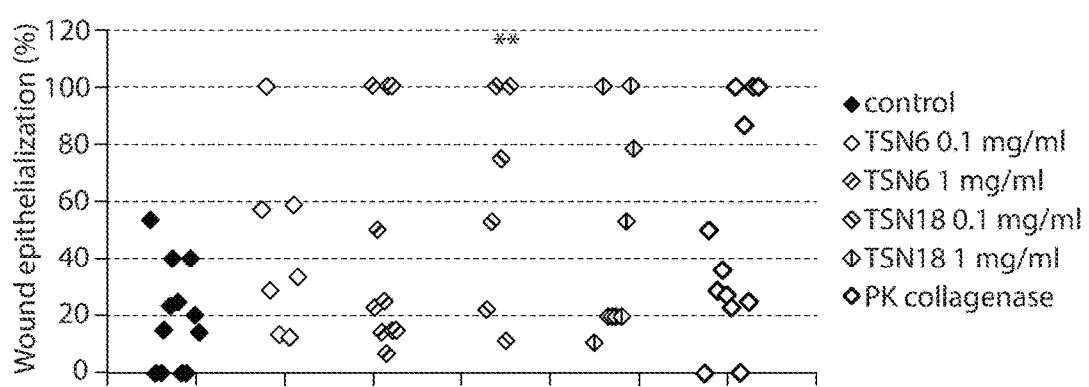
FIG. 9 shows ECM-derived peptides stimulate wound epithelialization in mice. Wounds were created and treated as described in FIG. 1. Wound epithelialization was measured at day 6 post wounding. ** indicate statistical significance of findings ($p<0.05$). Treatments from left to right: control; TSN6, 0.1 mg/ml; TSN6, 1 mg/ml; TSN18, 0.1 mg/ml; TSN18, 1 mg/ml; PK collagenase.

Modified wound scoring system. Tissues were collected as described herein and depicted in FIG. 6, sectioned and stained with Haematoxylin and eosin. Scores were assigned to each wound by an investigator in a blind manner.

| Score | Description |
|---|---|
| 1 | No epithelialization, no granulation tissue |
| 2 | No epithelialization, granulation tissue poorly formed |
| 3 | Complete epithelialization, granulation tissue poorly formed |
| 4 | Complete epithelialization, well-defined granulation tissue |

Several of the peptides, which have proven to be efficacious in the pre-clinical in vitro modeling experiments, similarly and markedly stimulate the cellular and tissue responses to injury, all of which fosters accelerated wound closure when compared to untreated control or collagenase-treated groups (c.f. FIGS. 7A-7L, 8 and 9). Indeed, peptide-treated groups (and, in particular those treated with TSN6, which is comprised of a coiled domain contained within multimerin), were markedly stimulated to heal wounds compared to untreated controls or groups treated with collagenase, alone, or other peptides.

REFERENCES CITED

1. Demidova-Rice T N, Hamblin M R, Herman I M. 2012. Acute and impaired wound healing: pathophysiology and current methods for drug delivery, part 1: normal and chronic wounds: biology, causes, and approaches to care. Adv Skin Wound Care. 25:304-14. PMID: 22713781.
2. Demidova-Rice T N, Hamblin M R, Herman I M. 2012. Acute and impaired wound healing: pathophysiology and current methods for drug delivery, part 2: role of growth factors in normal and pathological wound healing: therapeutic potential and methods of delivery. Adv Skin Wound Care. August; 25:349-70. PMID: 22820962.
3. Dulmovits B M, Herman I M. 2012. Microvascular remodeling and wound healing: A role for pericytes. Int J Biochem Cell Biol. 44: 1800-12. doi: 10.1016/j.biocel.2012.06.031. Epub June 28. PMID: 22750474.
4. Schultz G S, Davidson J, Kirsner R, Bornstein P and Herman I M. 2011. Dynamic Reciprocity in the Wound Microenvironment. Wound Repair Regen. (March-April; 19(2):134-48. doi: 10.1111/j.1524-475X.2011.00673.x. PMID:21362080.
5. Demidova-Rice T, Geevarghese A, Herman I M. Bioactive peptides derived from vascular endothelial cell extracellular matrices promote microvascular morphogenesis and wound healing in vitro. Wound Repair Regen. 2011 January-February; 19(1):59-70. doi: 10.1111/j.1524-475X.2010.00642.x. Epub 2010 Dec. 6.
6. Demidova-Rice T N, Wolf L, Deckenback J, Hamblin M R, Herman, I M. 2012. Human platelet-rich plasma- and extracellular matrix-derived peptides promote impaired cutaneous wound healing in vivo. PLoS One.; 7:e32146. Epub 2012 Feb. 23. PMID: 22384158.
7. Falanga V. 2005. Wound healing and its impairment in the diabetic foot. Lancet. 366:1736-1743. [PubMed]
8. Herman I M. Endothelial cell matrices modulate smooth muscle cell growth, contractile phenotype and sensitivity to heparin.Haemostasis. 1990; 20 Suppl 1:166-77.

9. Newcomb P M, Herman I M. Pericyte growth and contractile phenotype: modulation by endothelial-synthesized matrix and comparison with aortic smooth muscle. J Cell Physiol. 1993 May; 155(2):385-93. PMID: 8482730.
10. Herman I M, Castellot J J Jr. Regulation of vascular smooth muscle cell growth by endothelial-synthesized extracellular matrices. Arteriosclerosis. 1987 September-October; 7(5):463-9. PMID: 3675305

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject inventions are explicitly disclosed herein, the above specification is illustrative and not restrictive. Many variations of the inventions will become apparent to those skilled in the art upon review of this specification and the claims below. The full scope of the inventions should be determined by reference to the claims, along with their full scope of equivalents, and the specification, along with such variations.

The invention claimed is:

1. An isolated peptide comprising an amino acid sequence selected from the group consisting of SEQ ID NO:s 1 and 3-19, wherein the peptide is between 8 and 100 amino acids in length.

2. An isolated peptide comprising an amino acid sequence selected from the group consisting of SEQ ID NO:s 1 and 3-19, wherein the peptide does not comprise a full-length protein.

3. The isolated peptide of claim 2, wherein the peptide comprises not more than 50, 45, 40, 35, 30, 25 or 20 contiguous amino acid residues of the protein from which the peptide was derived.

4. The isolated peptide of claim 1, wherein the peptide consists of an amino acid sequence selected from the group consisting of SEQ ID NO:s 1 and 3-19.

5. A combinatorial peptide comprising an isolated peptide of claim 1 conjugated or fused to a second peptide or polypeptide.

6. A composition or article of manufacture comprising one or more of the isolated peptides of claim 1 and a carrier or excipient.

7. The composition or article of manufacture of claim 6, wherein the carrier or excipient is a pharmaceutically acceptable carrier or excipient.

8. The composition or article of manufacture of claim 6, wherein the one or more of the isolated peptides or one or more of the combinatorial peptides comprise protease cleavage sites, optionally wherein the protease cleavage sites are different in different peptides or combinatorial peptides.

9. The composition or article of manufacture of claim 6, wherein the one or more isolated peptides or one or more combinatorial peptides are anchored to a scaffold, which optionally is a bioerodible and non-immunogenic scaffold.

10. A method to promote wound healing in a subject in need thereof, comprising administering to the subject an effective amount of one or more of the isolated peptides of claim 1.

11. The method of claim 10, wherein the peptide consists of an amino acid sequence selected from the group consisting of SEQ ID NO:s 1 and 3-19.

12. The method of claim 10, wherein the peptide is administered in an amount effective to enhance the rate of migration of keratinocytes or endothelial cells, or a combination of keratinocytes and endothelial cells, towards a wound edge.

13. The method of claim 10, wherein the administration of the peptide results in an increase in the re-epithelialization of the wound.

14. The method of claim 10, wherein the administration of the peptide results in an increase in angiogenesis in or near the wound.

15. The method of claim 10, wherein the peptide is administered at a wound site.

16. The method of claim 10, wherein the wound is a thermal, chronic, acute or surgical wound.

17. The method of claim 10, further comprising administering to the subject a second agent.

18. The method of claim 17, wherein the second agent is a polypeptide.

19. The method of claim 17, wherein the second agent is a growth factor, cytokine, or enzyme.

20. The method of claim 17, wherein the second agent is a non-human collagenase.

21. The method of claim 20, wherein the non-human collagenase is bacterial collagenase.

22. The method of claim 10, wherein the subject is a mammalian subject.

23. The method of claim 22, wherein the mammalian subject is a human.

* * * * *